(12) United States Patent
Lanver et al.

(10) Patent No.: US 8,367,875 B2
(45) Date of Patent: Feb. 5, 2013

(54) PROCESS FOR THE PREPARATION OF M-SUBSTITUTED ALKYLTOLUENES BY ISOMERIZATION WITH IONIC LIQUIDS AS CATALYSTS

(75) Inventors: Andreas Lanver, Mannheim (DE); Klaus Ebel, Lampertheim (DE); Karl Beck, Östringen (DE); Ralf Pelzer, Fürstenberg (DE); Jörg Botzem, Limburgerhof (DE); Ulrich Griesbach, Mannheim (DE)

(73) Assignee: BASF SE, Ludwigshafen (DE)

( * ) Notice: Subject to any disclaimer, the term of this patent is extended or adjusted under 35 U.S.C. 154(b) by 178 days.

(21) Appl. No.: 13/024,786

(22) Filed: Feb. 10, 2011

(65) Prior Publication Data

US 2011/0196176 A1 Aug. 11, 2011

Related U.S. Application Data

(60) Provisional application No. 61/303,331, filed on Feb. 11, 2010.

(51) Int. Cl.
*C07C 45/45* (2006.01)
*C07C 5/22* (2006.01)
(52) U.S. Cl. .......................... 568/434; 585/477; 585/478
(58) Field of Classification Search .................. 568/434; 585/477, 478
See application file for complete search history.

(56) References Cited

U.S. PATENT DOCUMENTS

| 2,741,647 | A | * | 4/1956 | Mccaulay et al. ............ 585/478 |
| 4,298,438 | A | | 11/1981 | Degner et al. |
| 6,723,883 | B1 | | 4/2004 | Therre et al. |
| 2010/0081804 | A1 | | 4/2010 | Hoffer et al. |

FOREIGN PATENT DOCUMENTS

| DE | 2948455 A1 | 6/1981 |
| DE | 19949672 A1 | 4/2001 |
| DE | 102005049568 A1 | 4/2007 |
| EP | 0029995 A1 | 6/1981 |
| JP | 2738093 | 8/1991 |
| WO | WO-2010/108817 A1 | 9/2010 |
| WO | WO-2011/048012 A1 | 4/2011 |
| WO | WO-2011/048068 A2 | 4/2011 |
| WO | WO-2011/067386 A2 | 6/2011 |

OTHER PUBLICATIONS

Earle, M., et al., "Organic Synthesis," Ionic Liquids in Synthesis, Wiley-VCH, 2003, pp. 174-213.
Kovacic, P., et al., "Amination of *m*-Dialkylbenzenes with Trichloramine-Aluminum Chloride," Amination of *m*-Dialkylbenzenes, Mar. 1967, vol. 32, pp. 585-588.
Nesterova, T.N., et al., "Contributions of Enthalpy and Entropy Factors to Isomerization Equilibrium of Isopropyl- and Cyclohexylbenzenes," Russian Journal of Applied Chemistry, 1999, vol. 72, No. 11, pp. 1884-1890.
Olah, G.A., et al., "Boron, Aluminum, and Gallium Tris(trifluoromethanesulfonate) (Triflate): Effective New Friedel-Crafts Catalysts," J. Am. Chem. Soc., 1988, vol. 110, pp. 2560-2565.

* cited by examiner

*Primary Examiner* — Sikarl Witherspoon
(74) *Attorney, Agent, or Firm* — Connolly Bove Lodge & Hutz LLP

(57) ABSTRACT

The invention relates to a process for the preparation of m-substituted alkyltoluenes of the formula (I)

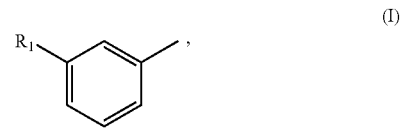

in which $R_1$ is $C_1$-$C_5$-alkyl, wherein a p-substituted alkyltoluene of the formula (II)

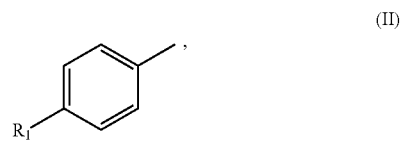

in which $R_1$ has the meaning given under formula (I), is isomerized in the presence of ionic liquids to give an m-substituted alkyltoluene of the formula (I). The m-substituted alkyltoluenes obtainable according to the invention are starting compounds for the preparation of fragrances and aroma substances.

18 Claims, No Drawings

PROCESS FOR THE PREPARATION OF M-SUBSTITUTED ALKYLTOLUENES BY ISOMERIZATION WITH IONIC LIQUIDS AS CATALYSTS

RELATED APPLICATIONS

Pursuant to 35 U.S.C. §119(e), this application claims benefit of U.S. Provisional Patent Application Ser. No. 61/303,331, filed on Feb. 11, 2010.

The present invention relates to a process for the preparation of m-substituted alkyltoluenes by isomerization of p-substituted alkyltoluenes. Substituted alkyltoluenes are important intermediates in the synthesis of fragrances of the 2-methyl-3-phenylpropanal type, such as e.g. Lysmeral® (BASF SE).

The ionic liquids used in the present invention comprising preferably an ammonium or imidazolium salt and a metal halide are described in the literature and are used inter alia in Friedel-Crafts alkylations (overview: P. Wasserscheid, T. Welton, Ionic Liquids in Synthesis, Wiley-VCH, 2003, p. 174ff.).

JP 2738093 describes the isomerization of 4-tert-butyltoluene to 3-tert-butyltoluene using $AlCl_3$ as catalyst. Compared with 4-tert-butyltoluene, 3-tert-butyltoluene is the thermodynamically more favorable product. Using $AlCl_3$ as catalyst an m/p isomer mixture is formed in the equilibrium with an m/p ratio of ca. 2/1 after a reaction time of 1 h at room temperature. Besides this equilibrium, there is a further competing equilibrium which leads to the formation of toluene and 3,5-di-tert-butyltoluene. In order to reduce the amount of 3,5-di-tert-butyltoluene, the addition of toluene (1 equivalent by weight) was described in JP 2738093.

Olah et al. has described the isomerization of 4-tert-butyl-toluene to 3-tert-butyltoluene and the alkylation of toluene with tert-butyl chloride (J. Am. Chem. Soc. 1988, 110, 2560-2565). Here, the catalysts used were tris(trifluoromethane-sulfonates) (triflates) of boron, aluminum and gallium [$B(OTf)_3$, $Ga(OTf)_3$ and $Al(OTf)_3$]. Here too, an equilibrium of 3-tert-butyltoluene/4-tert-butyltoluene of ca. 2/1 was established.

In the case of the industrial conversion of these processes, it is disadvantageous that the catalyst has to be separated off by means of a complex solid/liquid separating operation, or it has to be hydrolyzed by means of aqueous work-up. This produces a significant amount of chloride-containing waste and metal salts.

Compared with this, the process according to the invention allows m-substituted alkyltoluenes to be prepared efficiently by isomerization of p-substituted alkyltoluenes in the presence of ionic liquids. Advantages of the procedure according to the invention are:
1) separation off of the catalyst takes place by a technically less complex liquid/liquid separating operation;
2) the simple recyclability of the catalyst (since no aqueous work-up is required which destroys the catalyst in the case of solid $AlCl_3$);
3) the higher reaction rate of the catalysis as a result of ionic liquids compared to the catalysis with solid $AlCl_3$.

The present invention relates to a process for the preparation of alkyltoluenes substituted in the m position which can be obtained by isomerization of alkyltoluenes substituted in the p position. The isomerization takes place over ionic liquids as catalysts. The invention therefore provides a process for the preparation of m-substituted alkyltoluenes of the formula (I)

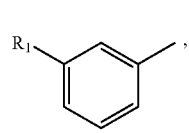
(I)

in which $R_1$ is $C_1$-$C_5$-alkyl, wherein a p-substituted alkyltoluene of the formula (II)

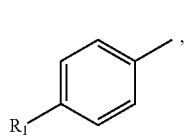
(II)

in which $R_1$ has the meaning given under formula (I), is isomerized in the presence of ionic liquids to give an m-substituted alkyltoluene of the formula (I).

Surprisingly, it has been found that ionic liquids catalyze the isomerization. Particularly suitable active ionic liquids are e.g. mixtures comprising the components (a) and (b), where
(a) is a first component of the formula $MX_3$ or $MX_2$, in which M is metal, such as e.g. Al, In, Zn, Fe, and X is halogen, such as e.g. chlorine, bromine or iodine, and
(b) is a second component selected from the following group: alkylammonium halide, imidazolium halide, pyridinium halide, phosphonium halide and mixtures of these compounds.

Preference is given to ionic liquids consisting of the mixture of the components (a) and (b).

The ratio of the two components (a)/(b) is >1/1.

The term "ionic liquid" refers to mixtures of the compounds (a) and (b) as described above which, after they have been homogenized and, optionally, melted, and cooled again, are liquid at a temperature of <100° C.

Preferred components (a) are $AlCl_3$, $AlBr_3$, $ZnCl_2$, $FeBr_3$ and $FeCl_3$. The component (a) is particularly preferably $AlCl_3$. The component (b) is preferably an imidazolium halide, such as e.g. imidazolium halide mono- or polysubstituted by $C_1$-$C_{10}$-alkyl, or an alkylammonium halide, such as e.g. alkylammonium halide di-, tri- or tetra-substituted by $C_1$-$C_6$-alkyl. Specific examples of particularly preferred compounds (b) are: 1-ethyl-3-methylimidazolium chloride, 1-butyl-3-methylimidazolium chloride, 1-hexyl-3-methylimidazolium chloride, 1-methylimidazolium chloride, triethylammonium chloride, trimethylammonium chloride, tetramethylammonium chloride, tetraethylammonium chloride, 1-butylpyridinium chloride and 1-methylpyridinium chloride is used.

The ratio of components (a)/(b) is >1/1. Preference is given to a ratio of >1/1 and <3/1. Particular preference is given to a ratio of >1.5/1 and <2.1/1. Very particular preference is given to a ratio of 2/1.

The catalyst is typically prepared by initially introducing component (a) or component (b) in a solvent and then metering in component (b) or component (a). After a reaction time of 1-12 hours at a temperature between 20-100° C., the ionic liquid is formed. The ionic liquid can either be separated off from the solvent phase by phase separation or be used in the isomerization complete as homogeneous solution of the catalyst in the solvent. Preferred solvents are aromatic hydrocarbons or chlorinated solvents. Particular preference is given to benzene, toluene, xylenes, mesitylene, 4-tert-butyltoluene and dichloromethane. Very particular preference is given to toluene.

The ionic liquid as catalyst is used in the isomerization in an amount of 0.1-100 mol %, based on the starting material of the formula (II). The preferred catalyst amount is 0.1-10 mol %. Particular preference is given to 0.5-5 mol %.

The isomerization takes place at temperatures between 0° C. and 100° C. Particular preference is given to temperatures between 10° C. and 50° C. The reaction times are 1 minute to 10 hours. Particular preference is given to reaction times between 30 minutes and 3 hours.

The isomerization can be carried out solvent-free or in a solvent. Suitable solvents are: toluene, xylenes, dichloromethane, chlorobenzene, hexane, heptane. Particular preference is given to toluene.

In the process according to the invention, a p-substituted alkyltoluene of the formula (II) is used as starting material. The alkyl radical $R_1$ is a $C_1$-$C_5$-alkyl radical, such as e.g. a methyl, ethyl, isopropyl, isobutyl, tert-butyl or isopentyl radical.

A preferred embodiment of the process according to the invention is one where the radical $R_1$ in the formula (II) is preferably $C_1$-$C_4$-alkyl, particularly preferably ethyl, isopropyl or tert-butyl.

Preferred starting materials for the isomerization are the following substrates: 4-tert-butyltoluene, 4-isopropyltoluene, 4-ethyltoluene. These produce the following m-isomers as main products (isomer ratio m/p>1/1) of the reaction: 3-tert-butyltoluene, 3-isopropyltoluene, 3-ethyltoluene. Particular preference is given to the substrate 4-tert-butyltoluene.

The reaction is generally carried out such that a mixture consisting of toluene, p-alkyl-substituted toluene and dialkyl-substituted toluene is reacted with the ionic liquid. When the reaction is complete, the phases are separated. The catalyst phase can be reused in the next batch. The second phase comprises the product of value (m-substituted alkyltoluene), and also toluene, the p-substituted alkyltoluene and a dialkyl-substituted alkyltoluene. For further work-up, this phase is subjected to an aqueous washing followed by a distillation, or is subjected directly to a distillation. The m-substituted alkyltoluenes are generally isolated by distillation. The components toluene and dialkyltoluenes that form during the reaction are by-products which can be separated off by distillation and returned to the isomerization reaction. By returning these products to the reaction mass, the equilibrium between the m-substituted alkyltoluene and the p-substituted alkyltoluene is reestablished again and again, as a result of which an increased fraction of the desired m-substituted product is obtained.

The invention further provides the preparation of the products of value of the formula (V) accessible from the m-substituted alkyltoluenes of the formula (I) by a reaction sequence consisting of oxidation, aldol condensation and hydrogenation

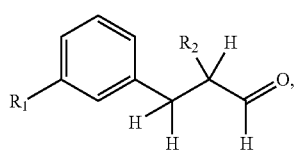
(V)

in which $R_1$ has the meaning given under formula (I) and $R_2$ is hydrogen or $C_1$-$C_5$-alkyl, preferably hydrogen or methyl, which are relevant as fragrances and aroma chemicals.

The alkyl radical $R_2$ is a $C_1$-$C_5$-alkyl radical, such as e.g. a methyl, ethyl, isopropyl, n-propyl, isobutyl, tert-butyl, n-butyl, n-pentyl or isopentyl radical. Preferably, the radical $R_2$ is hydrogen or methyl.

From the m-substituted alkyltoluenes of the formula (I) obtainable according to the invention

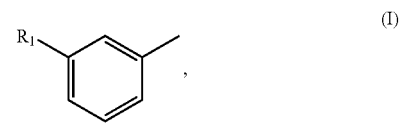
(I)

in which $R_1$ is $C_1$-$C_5$-alkyl, preferably ethyl, isopropyl or tert-butyl, it is possible, through oxidation by processes known per se (e.g. electrochemical oxidation of substituted toluenes to substituted benzaldehydes according to DE2948455), to form the m-alkyl-substituted benzaldehyde of the formula (III)

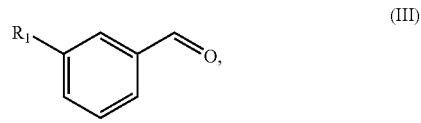
(III)

in which $R_1$ has the meaning given under formula (I). A subsequent aldol condensation of substituted benzaldehydes of the formula (III) with e.g. an aldehyde of the formula (IIIa)

(IIIa)

in which $R_2$ is hydrogen or $C_1$-$C_5$-alkyl, to give substituted cinnamaldehydes of the formula (IV) is described e.g. in DE19949672

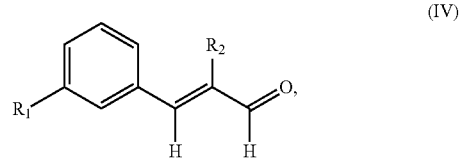
(IV)

in which $R_1$ has the meaning given under formula (III) and $R_2$ is hydrogen or $C_1$-$C_5$-alkyl, preferably hydrogen or methyl. The hydrogenation of substituted cinnamaldehydes of the formula (IV) to substituted phenylpropanals of the formula (V) is described e.g. in DE102005049568

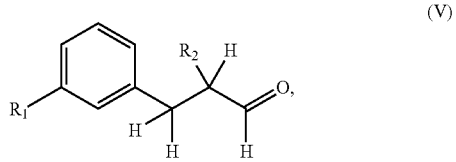

(V)

in which $R_1$ and $R_2$ have the meanings given under formula (IV).

Some of the aldehydes of the formula (V) obtained according to the process are known and some are new fragrances and aroma substances.

In the compounds of the type (III), (IV) and (V), $R_1$ is bonded to the phenyl ring in the m position and is $C_1$-$C_5$-alkyl, preferably $C_1$-$C_4$-alkyl, particularly preferably ethyl, isopropyl and tert-butyl, and $R_2$ is hydrogen or $C_1$-$C_5$-alkyl, preferably hydrogen or methyl. $R_1$ is very particularly preferably tert-butyl.

The invention is illustrated in more detail by the examples below without limiting it thereto. In the examples, all of the data in % are to be understood as meaning % by weight. (Abbreviations: BMIM=1,3-butylmethylimidazolium; EMIM=1,3-ethylmethylimidazolium; HMIM=1-methylimidazolium; TEA=triethylammonium; TMA=trimethylammonium; BuPy=1-butylpyridinium; m-TBT=m-tert-butyltoluene; p-TBT=p-tert-butyltoluene; o-TBT=o-tert-butyltoluene; DTBT=di-tert-butyltoluene; PhMe=toluene).

EXAMPLE 1

3500 g of toluene were initially introduced in a 7 l jacketed reactor and heated to 50° C., and then 175 g (1 mol) of 1,3-butylmethylimidazolium chloride were added. 267 g (2 mol) of aluminum chloride were added in portions over the course of 15 min. The mixture was then stirred for 1 h at 50° C. and for a further 1.5 h at 25° C. After phase separation, 875 g of a black-green catalyst phase consisting of BMIM [$Al_2Cl_7$] as 50.5% strength solution in toluene and 3281 g of a greenish toluene phase were obtained.

EXAMPLE 2

2500 g of toluene were initially introduced in a 7 l jacketed reactor and 267 g (2 mol) of aluminum chloride were added. Then, (1 mol) 138 g of triethylammonium chloride were added over the course of 10 min. The mixture was then stirred for 2 h at 25° C. and for 2 h at 45° C. After phase separation, 895 g of a black-green catalyst phase consisting of $Et_3NH$ [$Al_2Cl_7$] as 45.3% strength solution in toluene and 2008 g of a greenish toluene phase were obtained.

EXAMPLE 3

1807 g of toluene were initially introduced in a 7 l jacketed reactor and heated to 50° C. and 147 g (1 mol) of ethylmethylimidazolium chloride were added. 264 g (1.98 mol) of aluminum chloride were added in portions over the course of 15 min. The mixture was then stirred for 1 h at 50° C. and for a further 1.5 h at 25° C. After phase separation, 864 g of a black-green catalyst phase consisting of EMIM [$Al_2Cl_7$] as 47.6% strength solution in toluene and 1333 g of a greenish toluene phase were obtained.

EXAMPLE 4

437 g (4.7 mol) of toluene and 4.6 kg (31.3 mol) of 4-tert-butyltoluene were initially introduced in a 7 l jacketed reactor. $Et_3NH$ $Al_2Cl_7$ (45% strength in toluene; 3.2 mol % based on 4-tert-butyltoluene) was added and the mixture was stirred for 1 h at 20° C. After the end of the reaction, the phases were separated. As the lower phase, 631 g of the catalyst $Et_3NH$ $Al_2Cl_7$ (64% strength in toluene/3-tert-butyltoluene/4-tert-butyltoluene/3,5-di-tert-butyltoluene) were obtained. 5265 g of the product mixture (upper phase) were obtained.

Table 1 shows the composition of the upper phase.

EXAMPLES 5 TO 10

The reaction was carried out analogously to example 4. The catalyst ($Et_3NH$ $Al_2Cl_7$; 64% strength in toluene/3-tert-butyltoluene/4-tert-butyltoluene/3,5-di-tert-butyltoluene) separated off in example 4 was reused. 824 g of toluene and 4.1 kg of 4-tert-butyltoluene were used. The reaction was carried out analogously 6 times. Table 1 shows the composition of the upper phases.

TABLE 1

|  | Toluene [%] | m-TBT [%] | p-TBT [%] | o-TBT [%] | DTBT [%] |
|---|---|---|---|---|---|
| Example 4 | 20.98 | 43.07 | 21.31 | 0.08 | 11.81 |
| Example 5 | 22.18 | 43.99 | 21.70 | 0.08 | 11.67 |
| Example 6 | 21.53 | 43.18 | 21.25 | 0.08 | 11.50 |
| Example 7 | 21.47 | 42.86 | 21.09 | 0.07 | 11.41 |
| Example 8 | 21.37 | 43.38 | 21.36 | 0.08 | 11.54 |
| Example 9 | 21.47 | 43.07 | 21.55 | 0.08 | 11.65 |
| Example 10 | 21.76 | 43.65 | 21.60 | 0.08 | 11.64 |

EXAMPLES 11 TO 35

The reaction was carried out analogously to example 4. The catalysts used, the catalyst amounts, reaction times, temperatures and the use amounts of toluene were varied. Table 2 shows the experimental results, the abbreviation eq=equivalents and area % are area percentages of the gas chromatographic evaluation.

TABLE 2

| Ex. | Catalyst Substance mol % | PhMe [eq] | Time min | Temp ° C. | Toluene area % | m-TBT area % | p-TBT area % | DTBT area % |
|---|---|---|---|---|---|---|---|---|
| 11 | 1 | 5.7 | 1.4 | 30 | 25 | 59.44 | 26.12 | 12.74 | 1.61 |
| 12 | 1 | 13.2 | 1.4 | 30 | 25 | 54.58 | 29.00 | 14.26 | 2.09 |
| 13 | 1 | 13.2 | 1.4 | 140 | 25 | 59.39 | 25.77 | 12.58 | 1.66 |
| 14 | 1 | 1.9 | 1.4 | 30 | 25 | 59.30 | 26.43 | 12.65 | 1.52 |
| 15 | 1 | 2.4 | 2.9 | 30 | 2 | 74.06 | 17.22 | 8.20 | 0.50 |
| 16 | 2 | 2.3 | 1.4 | 30 | 25 | 58.44 | 1.28 | 40.09 | — |
| 17 | 3 | 1.9 | 1.4 | 30 | 25 | 58.51 | 1.28 | 40.07 | — |
| 18 | 4 | 2.1 | 1.4 | 30 | 25 | 58.00 | 1.29 | 40.53 | — |
| 19 | 5 | 2.7 | 1.4 | 30 | 25 | 58.06 | 1.29 | 40.49 | — |

TABLE 2-continued

| Ex. | Catalyst Substance | mol % | PhMe [eq] | Time min | Temp ° C. | Toluene area % | m-TBT area % | p-TBT area % | DTBT area % |
|---|---|---|---|---|---|---|---|---|---|
| 20 | 6 | 2.5 | 1.4 | 30 | 25 | 58.70 | 26.48 | 12.93 | 1.59 |
| 21 | 7 | 2.2 | 1.4 | 30 | 25 | 58.95 | 26.40 | 12.87 | 1.57 |
| 22 | 8 | 2.7 | 1.4 | 30 | 25 | 58.69 | 26.10 | 12.63 | 1.49 |
| 23 | 9 | 2.5 | 1.4 | 30 | 25 | 58.05 | 26.48 | 12.93 | 1.65 |
| 24 | 10 | 2.0 | 1.4 | 30 | 25 | 57.13 | 1.32 | 41.35 | — |
| 25 | 7 | 2.7 | 1.4 | 30 | 25 | 56.52 | 3.00 | 39.70 | 0.09 |
| 26 | 11 | 3.1 | 1.4 | 30 | 25 | 57.04 | 1.32 | 41.29 | — |
| 27 | 12 | 2.2 | 1.4 | 30 | 25 | 59.64 | 25.19 | 12.33 | 1.48 |
| 28 | 13 | 2.1 | 1.4 | 30 | 25 | 57.52 | 1.31 | 40.96 | — |
| 29 | 14 | 2.1 | 1.4 | 30 | 25 | 57.74 | 1.30 | 40.78 | — |
| 30 | 15 | 2.5 | 1.4 | 60 | 50 | 58.45 | 1.27 | 40.06 | — |
| 31 | 7 | 2.0 | 1.4 | 120 | 25 | 59.52 | 25.42 | 13.45 | 1.57 |
| 32 | 7 | 2.0 | 0.2 | 30 | 25 | 22.17 | 43.85 | 21.63 | 11.80 |
| 33 | 7 | 1.0 | 0.2 | 12 | 25 | 22.22 | 43.67 | 21.92 | 11.93 |
| 34 | 7 | 0.4 | 0.2 | 30 | 25 | 22.15 | 43.69 | 21.77 | 11.87 |
| 35 | 7 | 0.1 | 0.2 | 60 | 25 | 16.97 | 5.69 | 75.06 | 1.07 |

BMIM Al$_2$Cl$_7$ = 1;
EMIM OAc = 5;
BuPy Al$_2$Cl$_7$ = 9;
HMIM Al$_2$Cl$_7$ = 12;
BMIM AlCl$_4$ = 15.
HMIM Cl = 2;
EMIM Al$_2$Cl$_7$ = 6;
BMIM InCl$_4$ = 10;
HMIM AlCl$_4$ = 13;
BMIM Cl = 3;
TEA Al$_2$Cl$_7$ = 7;
EMIM InCl$_4$ = 11;
HMIM InCl$_4$ = 14;
EMIM Cl = 4
TMA Al$_2$Cl$_7$ = 8;

EXAMPLE 36

4.2 g of toluene and 3.0 g of 4-tert-butyltoluene were initially introduced and EMIM Al$_2$Cl$_7$ (45% strength in toluene; 3 mol % based on 4-tert-butyltoluene) were added and the mixture was stirred for 3 min at 20° C. The phases were separated and a sample was taken from the upper product-of-value phase and analyzed. The sample had the following composition: toluene 57%; 3-tert-butyltoluene 27%; 4-tert-butyltoluene 13%; 3,5-di-tert-butyltoluene 1.7%.

The invention claimed is:

1. A process for the preparation of m-substituted alkyltoluenes of the formula (I)

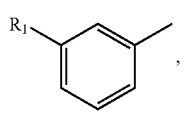

(I)

in which R$_1$ is C$_1$-C$_5$-alkyl, wherein a p-substituted alkyltoluene of the formula (II)

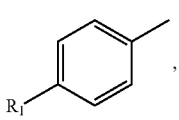

(II)

in which R$_1$ has the meaning given under formula (I), is isomerized in the presence of ionic liquids to give an m-substituted alkyltoluene of the formula (I).

2. The process according to claim 1, wherein ionic liquids are used comprising a mixture of the components (a) and (b), in which
  (a) is a first component of the formula MX$_3$ or MX$_2$, in which M is metal and X is halogen, and
  (b) is a second component selected from the group consisting of alkylammonium halide, imidazolium halide, pyridinium halide, phosphonium halide and mixtures of these compounds.

3. The process according to claim 2, wherein ionic liquids are used consisting of the components (a) and (b).

4. The process according to claim 2, wherein the ratio of components (a)/(b) is greater than 1/1.

5. The process according to claim 2, wherein ionic liquids are used in which the component (a) is AlCl$_3$, AlBr$_3$, ZnCl$_2$, FeBr$_3$.

6. The process according to claim 2, wherein ionic liquids are used in which the component (b) is imidazolium halide or alkylammonium halide.

7. The process according to claim 6, wherein, as component (b), 1-ethyl-3-methylimidazolium chloride, 1-butyl-3-methylimidazolium chloride, 1-hexyl-3-methylimidazolium chloride, 1-methylimidazolium chloride, triethylammonium chloride, trimethylammonium chloride, tetramethylammonium chloride, tetraethylammonium chloride, 1-butylpyridinium chloride or 1-methylpyridinium chloride is used.

8. The process according to claim 2, wherein the ratio of components (a)/(b) is greater than 1.5/1 and less than 2.1/1.

9. The process according to claim 1, wherein the isomerization takes place at a temperature between 0° C. and 100° C.

10. The process according to claim 1, wherein the isomerization is carried out in a solvent.

11. The process according to claim 1, wherein a p-substituted alkyltoluene of the formula (II)

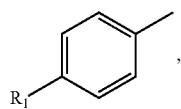

is used, in which $R_1$ is $C_1$-$C_4$-alkyl.

12. The process according to claim 11, wherein 4-tert-butyltoluene is selected as compound of the formula (II).

13. A process for the preparation of fragrances and aroma chemicals of the general formula (V)

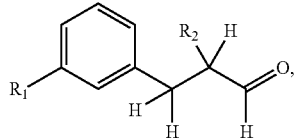

in which $R_1$ is $C_1$-$C_5$-alkyl, and $R_2$ is hydrogen or $C_1$-$C_5$-alkyl, comprising the stages a) isomerization of a p-substituted alkyltoluene of the formula (II)

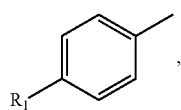

in which $R_1$ has the meaning given in claim 1, in the presence of ionic liquids to given an m-substituted alkyltoluene of the formula (I)

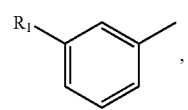

in which $R_1$ has the meanings given in claim 1, b) oxidation of the m-alkyl-substituted toluene of the formula (I) to give the m-alkyl-substituted benzaldehyde of the formula (III)

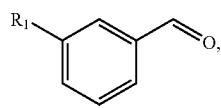

in which $R_1$ has the meaning given under formula (I), c) aldol condensation of the benzaldehyde of the formula (III) with an aldehyde of the formula (IIIa)

in which $R_2$ is hydrogen or $C_1$-$C_5$-alkyl, to give the cinnamaldehyde of the formula (IV)

(IV)

in which $R_1$ has the meaning given under formula (III) and $R_2$ has the meaning given under formula (IIIa), and d) hydrogenation of the cinnamaldehyde of the formula (IV) to give the alkyl-substituted phenylpropanal of the formula (V)

(V)

in which $R_1$ and $R_2$ have the meanings given under formula (IV).

14. The process according to claim 2, wherein ionic liquids are used in which the component (a) is $AlCl_3$.

15. The process according to claim 10, wherein the solvent is toluene, xylenes, dichloromethane, chlorobenzene, hexane or heptane, or mixtures of these solvents.

16. The process according to claim 11, wherein $R_1$ is ethyl, isopropyl, or tert-butyl.

17. The process according to claim 13, wherein $R_1$ is $C_1$-$C_4$-alkyl and $R_2$ is hydrogen or methyl.

18. The process according to claim 13, wherein $R_1$ is ethyl, isopropyl or tert-butyl.

* * * * *